US006451563B1

(12) United States Patent
Wittig et al.

(10) Patent No.: US 6,451,563 B1
(45) Date of Patent: Sep. 17, 2002

(54) METHOD FOR MAKING LINEAR, COVALENTLY CLOSED DNA CONSTRUCTS

(75) Inventors: Burghardt Wittig; Claas Junghans; Matthias Schroff, all of Berlin (DE)

(73) Assignee: Mologen Forschungs-, Entwicklungs- und Vertriebs GmbH, Berlin (DE)

( * ) Notice: Subject to any disclaimer, the term of this patent is extended or adjusted under 35 U.S.C. 154(b) by 0 days.

(21) Appl. No.: 09/503,799

(22) Filed: Feb. 14, 2000

Related U.S. Application Data

(63) Continuation-in-part of application No. PCT/EP99/04339, filed on Jun. 15, 1999.

(30) Foreign Application Priority Data

Jun. 15, 1998 (DE) .......................... 198 26 758

(51) Int. Cl.⁷ .................. C12P 19/34; C07H 21/04; C12N 9/12; C12N 9/16; C12N 15/00
(52) U.S. Cl. .................. 435/91.5; 435/41; 435/69.1; 435/91.1; 435/91.52; 435/194; 435/196; 435/91.53; 435/91.2; 435/320.1; 536/23.1; 536/24.1; 536/24.2; 536/24.33; 536/25.4
(58) Field of Search .................. 435/320.1, 6, 91.2, 435/91.1, 196, 194, 41, 69.1, 91.5, 91.53, 91.52; 536/23.1, 24.2, 24.3, 24.33, 25.4, 24.1

(56) References Cited

U.S. PATENT DOCUMENTS 5,859,226 A * 1/1999 Hunt et al. ............. 536/23.1

FOREIGN PATENT DOCUMENTS

| WO | WO 92/13963 | * | 8/1992 |
| WO | 9313216 | | 7/1993 |
| WO | WO 94/12633 | * | 6/1994 |
| WO | WO 98/21322 | * | 5/1998 |

OTHER PUBLICATIONS

Kilisch et al. Covalently linked sequencing primer linkers (slinkers) for sequence analysis of restriction fragments. Gene vol. 44, pp. 263–270, Dec. 1986.*

Roberts, RJ. Restricition and modification enzymes and their recognition sequences. vol. 13 Suppl. r165–r200, Dec. 1985.*

Berger and Kimmel. Guide to molecular cloning techniques. Methods in Enzymology. vol. 52, Academic Press, Inc. New York. pp. 307–661, Dec. 1987.*

* cited by examiner

*Primary Examiner*—Stephanie Zitomer
(74) *Attorney, Agent, or Firm*—Nils H. Ljungman & Associates

(57) ABSTRACT

A process to obtain linear double-stranded covalently closed DNA "dumbbell" constructs from plasmids by restriction digest, subsequent ligation with hairpin oligodesoxyribonucleotides, optionally in the presence of restriction enzyme, and a final digestion with endo- and exonucleolytic enzymes that degrade all contaminating polymeric DNA molecules but the desired construct. The invention also provides a process to obtain said dumbbell constructs employing endonuclease class II enzymes. Furthermore, the invention provides a process to obtain linear, covalently closed DNA molecules, such as plasmids, free from contamination by genomic DNA, by submitting the DNA preparation to a facultative endonucleolytic degradation step and an obligatory exonucleolytic degradation step.

23 Claims, No Drawings

SEQUENCE LISTING

<160> NUMBER OF SEQ ID NOS: 4

<210> SEQ ID NO 1
<211> LENGTH: 4397
<212> TYPE: DNA
<213> ORGANISM: Artificial Sequence
<220> FEATURE:
<223> OTHER INFORMATION: pUC 19 derivative, comprising a coding sequence
      for the modified enhanced green fluorescence protein from aquaeora
      victoria under control of cmv-promoter

<400> SEQUENCE: 1

```
tcttccgctt cctcgctcac tgactcgctg cgctcggtcg ttcggctgcg gcgagcggta      60
tcagctcact caaaggcggt aatacggtta tccacagaat cagggggataa cgcaggaaag     120 aacatgtgag caaaaggcca gcaaaaggcc aggaaccgta aaaaggccgc gttgctggcg     180 ttttttccata ggctccgccc ccctgacgag catcacaaaa atcgacgctc aagtcagagg    240
tggcgaaacc cgacaggact ataaagatac caggcgtttc ccccttggaag ctccctcgtg    300 cgctctcctg ttccgaccct gccgcttacc ggatacctgt ccgcctttct cccttcggga    360
agcgtggcgc tttctcatag ctcacgctgt aggtatctca gttcggtgta ggtcgttcgc    420
tccaagctgg gctgtgtgca cgaaccccccc gttcagcccg accgctgcgc cttatccggt    480
aactatcgtc ttgagtccaa cccggtaaga cacgacttat cgccactggc agcagccact    540
ggtaacagga ttagcagagc gaggtatgta ggcggtgcta cagagttctt gaagtggtgg    600
cctaactacg gctacactag aaggacagta tttggtatct gcgctctgct gaagccagtt    660
accttcggaa aaagagttgg tagctcttga tccggcaaac aaaccaccgc tggtagcggt    720
ggtttttttg tttgcaagca gcagattacg cgcagaaaaa aaggatctca agaagatcct    780
ttgatctttt ctacggggtc tgacgctcag tggaacgaaa actcacgtta agggattttg    840
gtcatgagat tatcaaaaag gatcttcacc tagatccttt taaattaaaa atgaagtttt    900
aaatcaatct aaagtatata tgagtaaact tggtctgaca gttaccaatg cttaatcagt    960
gaggcaccta tctcagcgat ctgtctattt cgttcatcca tagttgcctg actccccgtc    1020
gtgtagataa ctacgatacg ggagggctta ccatctggcc ccagtgctgc aatgataccg    1080
cgagacccac gctcaccggc tccagattta tcagcaataa accagccagc cggaagggcc    1140
```

-continued

```
gagcgcagaa gtggtcctgc aactttatcc gcctccatcc agtctattaa ttgttgccgg      1200
gaagctagag taagtagttc gccagttaat agtttgcgca acgttgttgc cattgctaca      1260
ggcatcgtgg tgtcacgctc gtcgtttggt atggcttcat tcagctccgg ttcccaacga      1320
tcaaggcgag ttacatgatc ccccatgttg tgcaaaaaag cggttagctc cttcggtcct      1380
ccgatcgttg tcagaagtaa gttggccgca gtgttatcac tcatggttat ggcagcactg      1440
cataattctc ttactgtcat gccatccgta agatgctttt ctgtgactgg tgagtactca      1500
accaagtcat tctgagaata gtgtatgcgg cgaccgagtt gctcttgccc ggcgtcaata      1560
cgggataata ccgcgccaca tagcagaact ttaaaagtgc tcatcattgg aaaacgttct      1620
tcggggcgaa aactctcaag gatcttaccg ctgttgagat ccagttcgat gtaacccact      1680
cgtgcaccca actgatcttc agcatctttt actttcacca gcgtttctgg gtgagcaaaa      1740
acaggaaggc aaaatgccgc aaaaaaggga ataaggcga cacggaaatg ttgaatactc      1800
atactcttcc ttttcaata ttattgaagc atttatcagg gttattgtct catgagcgga      1860
tacatatttg aatgtattta gaaaaataaa caaatagggg ttccgcgcac atttccccga      1920
aaagtgccac ctgacgtcta agaaaccatt attatcatga cattaaccta taaaaatagg      1980
cgtatcacga ggccctttcg tctcgcgcgt ttcggtgatg acggtgaaaa cctctgacac      2040
atgcagctcc cggagacggt cacagcttgt ctgtaagcgg atgccgggag cagacaagcc      2100
cgtcagggcg cgtcagcggg tgttggcggg tgtcggggct ggcttaacta tgcggcatca      2160
gagcagattg tactgagagt gcaccatatg cggtgtgaaa taccgcacag atgcgtaagg      2220
agaaaatacc gcatcaggcg ccattcgcca ttcaggctgc gcaactgttg ggaagggcga      2280
tcggtgcggg cctcttcgct attacgccag ctggcgaaag gggatgtgc tgcaaggcga      2340 ttaagttggg taacgccagg gttttcccag tcacgacgtt gtaaaacgac ggccagtgcc      2400
aagcttgcga attctggatc cgctagctta accgtattac cgccatgcat tagttattaa      2460
tagtaatcaa ttacggggtc attagttcat agcccatata tggagttccg cgttacataa      2520
cttacggtaa atggcccgcc tggctgaccg cccaacgacc cccgcccatt gacgtcaata      2580
atgacgtatg ttcccatagt aacgccaata gggactttcc attgacgtca atgggtggag      2640
tatttacggt aaactgccca cttggcagta catcaagtgt atcatatgcc aagtacgccc      2700
cctattgacg tcaatgacgg taaatggccc gcctggcatt atgcccagta catgacctta      2760
tgggactttc ctacttggca gtacatctac gtattagtca tcgctattac catggtgatg      2820
cggttttggc agtacatcaa tgggcgtgga tagcggtttg actcacgggg atttccaagt      2880
ctccacccca ttgacgtcaa tgggagtttg ttttggcacc aaaatcaacg ggactttcca      2940
aaatgtcgta caactccgcc ccattgacg caaatgggcg gtaggcgtgt acggtgggag      3000
gtctatataa gcagagctgg tttagtgaac cgtcagatgg taccgaagcc gctagcgcta      3060
ccggtcgcca ccatggtgag caagggcgag gagctgttca ccggggtggt gcccatcctg      3120
gtcgagctgg acggcgacgt aaacggccac aagttcagcg tgtccggcga gggcgagggc      3180
gatgccacct acggcaagct gaccctgaag ttcatctgca ccaccggcaa gctgcccgtg      3240
ccctggccca cctcgtgac cacccctgacc tacggcgtgc agtgcttcag ccgctacccc      3300
gaccacatga agcagcacga cttcttcaag tccgccatgc ccgaaggcta cgtccaggag      3360
cgcaccatct tcttcaagga cgacggcaac tacaagaccc gcgccgaggt gaagttcgag      3420
ggcgacaccc tggtgaaccg catcgagctg aagggcatcg acttcaagga ggacggcaac      3480
atcctggggc acaagctgga gtacaactac aacagccaca acgtctatat catggccgac      3540
```

```
aagcagaaga acggcatcaa ggtgaacttc aagatccgcc acaacatcga ggacggcagc   3600
gtgcagctcg ccgaccacta ccagcagaac accccatcg gcgacggccc cgtgctgctg    3660
cccgacaacc actacctgag cacccagtcc gccctgagca agacccccaa cgagaagcgc   3720
gatcacatgg tcctgctgga gttcgtgacc gccgccggga tcactctcgg catggacgag   3780
ctgtacaaga gctcataatc agccatacca catttgtaga ggttttactt gctttaaaaa   3840
acctcccaca cctcccctg aacctgaaac ataaaatgaa tgcaattctt gttgttaact    3900
tgtttattgc agcttataat ggttacaaat aaagcaatag catcacaaat ttcacaaata   3960
aagcattttt ttcactgcat tctagttgtg gtttgtccaa actcatcaat gtatcttaac   4020
gcgaattgtt gttgttaact tgtttattgc agcttataat ggttacaaat aaagcaatag   4080
catcacaaat ttcacaaata aagcattttt ttcactgcat tctagttgtg gtttgtccaa   4140
actcatcaat gtatcttaac gcgaattcgt aatcatggtc atagctgttt cctgtgtgaa   4200
attgttatcc gctcacaatt ccacacaaca tacgagccgg aagcataaag tgtaaagcct   4260
ggggtgccta atgagtgagc taactcacat taattgcgtt gcgctcactg cccgctttcc   4320
agtcgggaaa cctgtcgtgc cagctgcatt aatgaatcgg ccaacgcgcg gggagaggcg   4380
gtttgcgtat tgggcgc                                                 4397

<210> SEQ ID NO 2
<211> LENGTH: 4278
<212> TYPE: DNA
<213> ORGANISM: Artificial Sequence
<220> FEATURE:
<223> OTHER INFORMATION: pUC 19 derivative, comprising a coding sequence
      for the modified enhanced green fluorescence protein from aquaeora
      victoria under control of cmv-promoter

<400> SEQUENCE: 2
tcttccgctt cctcgctcac tgactcgctg cgctcggtcg ttcggctgcg gcgagcggta   60
tcagctcact caaaggcggt aatacggtta tccacagaat caggggataa cgcaggaaag   120
aacatgtgag caaaaggcca gcaaaaggcc aggaaccgta aaaaggccgc gttgctggcg   180 ttttccata ggctccgccc ccctgacgag catcacaaaa atcgacgctc aagtcagagg    240
tggcgaaacc cgacaggact ataaagatac caggcgtttc cccctggaag ctccctcgtg   300
cgctctcctg ttccgaccct gccgcttacc ggatacctgt ccgcctttct cccttcggga   360
agcgtggcgc tttctcatag ctcacgctgt aggtatctca gttcggtgta ggtcgttcgc   420
tccaagctgg gctgtgtgca cgaaccccc gttcagcccg accgctgcgc cttatccggt    480
aactatcgtc ttgagtccaa cccggtaaga cacgacttat cgccactggc agcagccact   540
ggtaacagga ttagcagagc gaggtatgta ggcggtgcta cagagttctt gaagtggtgg   600
cctaactacg gctacactag aaggacagta tttggtatct gcgctctgct gaagccagtt   660
accttcggaa aaagagttgg tagctcttga tccggcaaac aaaccaccgc tggtagcggt   720
ggtttttttg tttgcaagca gcagattacg cgcagaaaaa aaggatctca agaagatcct   780
ttgatctttt ctacggggtc tgacgctcag tggaacgaaa actcacgtta agggattttg   840
gtcatgagat tatcaaaaag gatcttcacc tagatccttt taaattaaaa atgaagtttt   900
aaatcaatct aaagtatata tgagtaaact tggtctgaca gttaccaatg cttaatcagt   960
gaggcaccta tctcagcgat ctgtctattt cgttcatcca tagttgcctg actccccgtc   1020
gtgtagataa ctacgatacg ggagggctta ccatctggcc ccagtgctgc aatgataccg   1080
```

-continued

```
cgagacccac gctcaccggc tccagattta tcagcaataa accagccagc cggaagggcc    1140
gagcgcagaa gtggtcctgc aactttatcc gcctccatcc agtctattaa ttgttgccgg    1200
gaagctagag taagtagttc gccagttaat agtttgcgca acgttgttgc cattgctaca    1260
ggcatcgtgg tgtcacgctc gtcgtttggt atggcttcat tcagctccgg ttcccaacga    1320
tcaaggcgag ttacatgatc ccccatgttg tgcaaaaaag cggttagctc cttcggtcct    1380
ccgatcgttg tcagaagtaa gttggccgca gtgttatcac tcatggttat ggcagcactg    1440
cataattctc ttactgtcat gccatccgta agatgctttt ctgtgactgg tgagtactca    1500
accaagtcat tctgagaata gtgtatgcgg cgaccgagtt gctcttgccc ggcgtcaata    1560
cgggataata ccgcgccaca tagcagaact ttaaaagtgc tcatcattgg aaaacgttct    1620
tcggggcgaa aactctcaag gatcttaccg ctgttgagat ccagttcgat gtaacccact    1680
cgtgcaccca actgatcttc agcatctttt actttcacca gcgtttctgg gtgagcaaaa    1740
acaggaaggc aaaatgccgc aaaaaaggga ataagggcga cacggaaatg ttgaatactc    1800
atactcttcc tttttcaata ttattgaagc atttatcagg gttattgtct catgagcgga    1860
tacatatttg aatgtattta gaaaaataaa caaataggggg ttccgcgcac atttccccga    1920
aaagtgccac ctgacgtcta agaaaccatt attatcatga cattaaccta taaaaatagg    1980
cgtatcacga ggccctttcg tctcgcgcgt ttcggtgatg acgtgaaaa cctctgacac    2040 atgcagctcc cggagacggt cacagcttgt ctgtaagcgg atgccgggag cagacaagcc    2100
cgtcagggcg cgtcagcggg tgttggcggg tgtcggggct ggcttaacta tgcggcatca    2160
gagcagattg tactgagagt gcaccatatg cggtgtgaaa taccgcacag atgcgtaagg    2220
agaaaatacc gcatcaggcg ccattcgcca ttcaggctgc gcaactgttg ggaagggcga    2280
tcggtgcggg cctcttcgct attacgccag ctggcgaaag gggatgtgc tgcaaggcga    2340 ttaagttggg taacgccagg gttttcccag tcacgacgtt gtaaaacgac ggccagtgcc    2400
aagcttggtc tccccctgga tccgctagct taaccgtatt accgccatgc attagttatt    2460
aatagtaatc aattacgggg tcattagttc atagcccata tatggagttc cgcgttacat    2520
aacttacggt aaatggcccg cctggctgac cgcccaacga cccccgccca ttgacgtcaa    2580
taatgacgta tgttcccata gtaacgccaa tagggacttt ccattgacgt caatgggtgg    2640
agtatttacg gtaaactgcc cacttggcag tacatcaagt gtatcatatg ccaagtacgc    2700
cccctattga cgtcaatgac ggtaaatggc ccgcctggca ttatgcccag tacatgacct    2760
tatgggactt tcctacttgg cagtacatct acgtattagt catcgctatt accatggtga    2820
tgcggttttg gcagtacatc aatgggcgtg gatagcggtt tgactcacgg ggatttccaa    2880
gtctccaccc cattgacgtc aatgggagtt tgttttggca ccaaaatcaa cgggactttc    2940
caaaatgtcg taacaactcc gccccattga cgcaaatggg cggtaggcgt gtacggtggg    3000
aggtctatat aagcagagct ggtttagtga accgtcagat ggtaccgaag ccgctagcgc    3060
taccggtcgc caccatggtg agcaagggcg aggagctgtt caccggggtg gtgcccatcc    3120
tggtcgagct ggacggcgac gtaaacggcc acaagttcag cgtgtccggc gagggcgagg    3180
gcgatgccac ctacggcaag ctgaccctga agttcatctg caccaccggc aagctgcccg    3240
tgccctggcc caccctcgtg accaccctga cctacggcgt gcagtgcttc agccgctacc    3300
ccgaccacat gaagcagcac gacttcttca gtccgccat gcccgaaggc tacgtccagg    3360
agcgcaccat cttcttcaag gacgacggca actacaagac ccgcgccgag gtgaagttcg    3420
agggcgacac cctggtgaac cgcatcgagc tgaagggcat cgacttcaag gaggacggca    3480
```

```
acatcctggg gcacaagctg gagtacaact acaacagcca caacgtctat atcatggccg    3540
acaagcagaa gaacggcatc aaggtgaact tcaagatccg ccacaacatc gaggacggca    3600
gcgtgcagct cgccgaccac taccagcaga acaccccat cggcgacggc cccgtgctgc    3660
tgcccgacaa ccactacctg agcacccagt ccgccctgag caaagacccc aacgagaagc    3720
gcgatcacat ggtcctgctg gagttcgtga ccgccgccgg gatcactctc ggcatggacg    3780
agctgtacaa gtgagctcat aatcagccat accacatttg tagaggtttt acttgcttta    3840
aaaaacctcc cacacctccc cctgaacctg aaacataaaa tgaatgcaat tgttgttgtt    3900
aacttgttta ttgcagctta taatggttac aaataaagca atagcatcac aaatttcaca    3960
aataaagcat tttttcact gcattctagt tgtggtttgt ccaaactcat caatgtatct     4020
taacgcgaat tcaggggag acccaattcg taatcatggt catagctgtt tcctgtgtga     4080
aattgttatc cgctcacaat tccacacaac atacgagccg gaagcataaa gtgtaaagcc    4140
tggggtgcct aatgagtgag ctaactcaca ttaattgcgt tgcgctcact gcccgctttc    4200
cagtcgggaa acctgtcgtg ccagctgcat taatgaatcg gccaacgcgc ggggagaggc    4260
ggtttgcgta ttgggcgc                                                  4278

<210> SEQ ID NO 3
<211> LENGTH: 25
<212> TYPE: DNA
<213> ORGANISM: Artificial Sequence
<220> FEATURE:
<223> OTHER INFORMATION: oligodinucleotide 1

<400> SEQUENCE: 3
aattggccgg ccgtttcggc cggcc                                          25

<210> SEQ ID NO 4
<211> LENGTH: 20
<212> TYPE: DNA
<213> ORGANISM: Artificial Sequence
<220> FEATURE:
<223> OTHER INFORMATION: oligodinucleotide 2

<400> SEQUENCE: 4
aggggtccag ttttctggac                                                20
```

METHOD FOR MAKING LINEAR, COVALENTLY CLOSED DNA CONSTRUCTS

CONTINUING APPLICATION DATA

This application is a Continuation-in-Part Application of International Application No. PCT/EP99/04339, filed on Jun. 15, 1999, which claims priority from Federal Republic of Germany Patent Application No. 198 26 758.4, filed on Jun. 15, 1998. International Application No. PCT/EP99/04339 was pending as of the filing date of the present application. The U.S. was an elected state in International Application No. PCT/EP99/04339.

BACKGROUND OF THE INVENTION

1. Field of the Invention

The present invention relates to the synthesis of a linear, double-stranded, covalently closed DNA molecule that can be used as a vector for gene therapy. More generally, the present invention also relates to a method of obtaining preparations of DNA molecules essentially free of contamination by genomic DNA originating from organisms employed in the making of the DNA molecules.

2. Background Information

Gene therapy and genetic vaccination are modern molecular approaches promising to change the way of future medical practice. Despite the great expectations inspired by these methods, however, some basic problems will have to be solved before these methods find general clinical acceptance.

Both gene therapy and genetic vaccination need methods to transfer genetic information into cells or tissues of a patient and to subsequently express the transferred information within those cells. There are safety, efficacy, and specificity issues associated with this transfer process and the transfer means employed. Generally speaking, viral transfer means are very efficient and specific but may be a cause for concern regarding both epidemiological and immunological issues. Non-viral transfer means such as naked DNA are considered to be much safer regarding possible reversion to pathogenicity, but may offer less efficacy and specificity. These issues are discussed, and some possible solutions offered, in our application WO 98/21322, the disclosure of which is incorporated herein by reference. The main aspect of Application No. WO 98/21322 is a minimalistic vector construct consisting mainly of linear double-stranded DNA, which is covalently closed by short oligodesoxyribonucleotide loops to essentially prevent exonucleolytic degradation and to allow attachment of specificity-inducing moieties. This construct will be referred to within the present specification also as, for example, a dumbbell expression construct, a dumbbell construct, and/or a dumbbell-shaped construct.

Several methods are known or can be fashioned without inventive activity in order to make such constructs. One can amplify the expression cassette forming the main, double-stranded part of the dumbbell construct by polymerase chain reaction (PCR), subsequently digest the amplified fragment by means of restriction enzymes, leaving overlapping ends, and ligate short hairpin oligonucleotides to the ends of the digested amplification fragments. Thereby, one will obtain dumbbell-shaped constructs that are essentially easily purified by HPLC on a large scale. The use of heat-stable or thermostable polymerases, however, makes the process uneconomical and gives rise to impurities in the product due to the high error rate of the polymerase. Alternatively, the main part of the construct can be amplified as part of a bacterial plasmid by fermentation, cut out from the plasmid backbone by restriction digest, and be ligated to hairpin oligonucleotides as described above. This leaves the desired product contaminated by backbone sequences, the removal of which is one main objective of making the minimalistic dumbbell constructs described in the present application. The backbone contamination can be removed by chromatography, electrophoresis, or other methods based on size. Since both vector backbone and expression cassette may be, and in practice often are, in the same size range—that is, between approximately 1.5 kilobasepairs and approximately 5 kilobasepairs, this separation based on size differences can be difficult and often renders suboptimal results. Therefore, methods are needed to obtain the desired constructs in an essentially easy, economical process.

OBJECT OF THE INVENTION

One object of the present invention may be to provide a process to obtain linear double-stranded covalently closed DNA "dumbbell" constructs from plasmids by restriction digest, subsequent ligation with hairpin oligodesoxyribonucleotides, optionally in the presence of restriction enzyme, and a final digest with endo- and exo-nucleolytic enzymes that degrade essentially all contaminating polymeric DNA molecules but the desired construct. Another object of the present invention may be to provide a process to obtain said dumbbell constructs employing endonuclease class II enzymes, recognizing non-palindromic sequences, and having the restriction site generate overlapping ends away from the enzyme recognition site. Furthermore, yet another object of the invention may be to provide a process to obtain linear, covalently closed DNA molecules, such as plasmids, essentially free from contamination by genomic DNA, by submitting the DNA preparation to a facultative endonucleolytic degradation step and an obligatory exonucleolytic degradation step.

SUMMARY OF THE INVENTION

According to the present invention, the DNA molecule forming the main, double-stranded part of the desired expression cassette dumbbell construct may be amplified by fermentation as part of a bacterial plasmid. The DNA molecule is isolated from the plasmid, on or in which it can be contained as a single or multiple copy within the plasmid sequence. Subsequently, the DNA molecule may be cut from the vector backbone by restriction endonucleases that may leave essentially short single overlaps at the restriction ends, preferably of three or more nucleotides in length.

In the next step, the resulting mix of expression cassette construct and vector backbone may be reacted in the presence of a DNA ligase with essentially short, hairpin-forming oligodesoxyribonucleotides that may comprise a single-stranded overlap hybridizing to the overlap generated by the restriction enzyme, resulting in a covalently closed single-stranded molecule with oligonucleotide loops at both ends. According to the invention, the resulting mix of dumbbell-shaped expression construct and backbone sequences, at least some of which backbone sequences may be in dumbbell form also, may be reacted with a restriction endonuclease that cuts only the backbone sequence and the recognition sequence that is not provided on the dumbbell expression construct. This endonuclease digest renders a mix of covalently closed molecules of the desired product, as well as digested backbone molecules and contaminating sequences with open 5' hydroxyl ends and 3' hydroxyl ends.

This mixture is subsequently submitted to extensive exonuclease digestion. The use of the exonuclease activity of bacteriophage T4 or T7 DNA polymerases was found, in at least one embodiment of the present invention, to be the best mode of executing this step of exonuclease digestion because of the essentially high specificity and processivity of these enzymes. However, any other specifically exonucleolytic activity can be employed to practice at least one possible embodiment of the present invention. The resulting digestion product is a mixture of the desired dumbbell construct, enzymes and buffer components, and desoxynucleotide monomers. From this mixture, the desired product can be purified essentially easy in a single and simple chromatographic step.

The main class of restriction enzymes used in molecular biology is endonuclease class I. These enzymes recognize short palindromic sequences and cut within the recognition site. These enzymes give very practical results when the products are to be used compatibly in cloning experiments. In the ligation described above, however, they may offer a serious drawback. The palindromic overlap generated by the enzyme can lead to reactions between restriction fragments, which reactions are referred to in the present specification as intra- or inter-polymeric reactions. The desired reaction, however, is a polymer-to-oligomer reaction. The former type of reaction—that is, intra- or inter-polymeric reactions—can be suppressed by an essentially large excess of hairpin oligomer, which in turn leads to the formation of hairpin dimers.

According to another aspect of the invention, this problem—that is, the problem of intra- or inter-polymeric reactions between or among restriction fragments—can be avoided in at least two ways. Firstly, hybridizing overlaps from two different recognition sites can be employed that do not generate, reconstitute, or reconstruct a palindromic sequence upon reaction between a polymer and an oligomer molecule, but instead may regenerate the in situ respective recognition site if hairpin dimers or polymeric dimers are formed. Both latter species—that is, both hairpin dimers and polymeric dimers—may be re-digested in the presence of ligase. Because hairpin-polymer ligation products do not form a palindromic site and are not re-digested, they may accumulate during the course of the reaction. One example of this strategy is the usage of an EcoRI site (G'AATTC, where the symbol "'" signifies the cut site, overlap AATT) to cut out or cleave the desired sequence from the plasmid and the use of an AATTG sequence for the 5' end of the hairpin, where AATT is the overlap sequence and G the first base of the double-stranded stem. Ligation of the plasmid fragment and the oligonucleotide may render or result in a ligation product with sequence GAATTG, which is not cut by any class I enzyme. If two ends of the plasmid religate, they can, in at least one possible embodiment of the present invention, be re-cut by EcoRI in situ, and an oligo dimer can be re-digested by MunI in situ (recognition sequence CAATTG).

Secondly, according to another aspect of the invention, the aforementioned problem of the need to employ a large excess of hairpin oligomer can be avoided by employing class II restriction endonucleases, which recognize non-palindromic sequences and cut away from their recognition site (see Butkus et al., "A New Restriction Endonuclease Eco31I Recognizing a Non-Palindromic Sequence," *Biochim. Biophys. Acta* Dec. 18, 1985; 826(4): 208–12, which publication is hereby incorporated by reference into this application). Many of these enzymes can be obtained from numerous commercial sources (for example, MBI-Fermentas, Vilnius, Lithuania, and New England Biolabs, Massachusetts, USA). The resulting ligation strategy employs hairpin oligonucleotides with a non-palindromic overlap. These molecules cannot ligate with one another and thus their active concentration in the ligation reaction diminishes through ligation to the vector fragment only. Consequently, the hairpin concentration leading to essentially exclusively monomeric fragment dumbbell products is much lower than the concentration resulting from employing palindromic sequences. Further improvement of the product quality can be achieved by adding a class II restriction enzyme to the ligation reaction in situ, which leads to re-digestion of inadvertently formed dimers.

According to yet another aspect of the invention, the digestion with a nonspecific exonuclease of preparations of covalently closed DNA obtained by fermentation can be used to purify such DNA preparations. This achieves an essentially great improvement over existing methods of purifying biotechnologically obtained DNA. The quality specifications given by one leading provider of so-called GMP-grade DNA give as release criteria the content of "host DNA <5%" (source: online catalog of Qiagen GmbH, which catalog is hereby incorporated by reference into this specification, entry as of Jun. 11, 1999, having the following URL or Internet link: http://www.giagen.com/catalog/ chapter 12/chap 12b.asp). It may be expected that such an essentially high degree of contamination will be the cause of calls for improvement.

Therefore, the present invention also may extend to a purification process for a preparation of any covalently closed DNA, such as a plasmid, derived from fermentative processes in prokaryotic or eukaryotic hosts. In at least one possible embodiment of the present invention, this process entails a digestion step using an exonuclease. Additionally, endonucleases can be added to digest the host genomic DNA; these endonucleases must not find an operable recognition site on the molecule to be purified. Preferably, a plurality of endonucleases is used. Anyone skilled in the art will be able to find or determine a number of suitable restriction enzymes using any of many available DNA sequence analysis computer programs (for example, see the MacMolly Tetra package for Apple Macintosh, the details of which package are hereby incorporated by reference into this application, available free at the following URL or Internet link: http://www.Mologen.com). The size of the bacterial genome makes it very likely that any endonuclease will find numerous sites on the bacterial genome; statistically, a six-basepair recognition site is contained about 250 times in a one-megabasepair genome. In any event, the genomic DNA may be expected to be fragmented by shear forces during preparation, so that the additional endonuclease digestion should serve only to accelerate the subsequent exonucleolytic step.

The above-discussed embodiments of the present invention will be described further hereinbelow with reference to the accompanying examples. When the word "invention" is used in this specification, the word "invention" includes "inventions", that is, the plural of "invention". By stating "invention", Applicants do not in any way admit that the present application does not include more than one patentably and non-obviously distinct invention. Applicants maintain that this application may include more than one patentably and non-obviously distinct invention. Applicants hereby assert that the disclosure of this application may include more than one invention, and, in the event that there is more than one invention, that these inventions may be patentable and non-obvious one with respect to the other.

DESCRIPTION OF THE PREFERRED EMBODIMENT

The following examples illustrate at least one possible embodiment of the present invention.

Example 1

1 mg of Plasmid pG-EGFP is digested to completion by incubation with EcoRI. The resulting fragments are ligated with 1 mg of 5'-phosphorylated desoxyoligoribonucleotide AATTGGCCGGCCGTTTCGGCCGGCC (TIB Molbiol, Berlin) in the presence of 100 U T4 DNA-Ligase (MBI-Fermentas, Vilnius, Lithuania) and 50 u restriction endonucleases MunI and EcoRI (MBI-Fermentas, Vilnius, Lithuania) in 5 ml reaction buffer at 37° C. overnight. The reaction is stopped by heating to 70° C. The resulting mixture of nucleic acids is concentrated and treated with 100 U restriction endonuclease HindIII and 100 U T7 DNA polymerase for one hour in the absence of desoxyribonucleotides. The resulting crude product is purified by chromatography on an anionic exchange column (Merck EMD-DMAE, sodium phosphate pH 7.0, 0–1 M NaCl) and obtained free of contamination by vector backbone, as assayed by PCR.

Example 2

1 mg of Plasmid pMol-EGFP is digested to completion by incubation with Eco31I. The resulting fragments are ligated with 50 µg of 5'-phosphorylated desoxyoligoribonucleotide AGGGGTCCAG TTTTCTGGAC (TIB Molbiol, Berlin) in the presence of 20 U T4 DNA-Ligase (MBI-Fermentas, Vilnius, Lithuania) and 50 u restriction endonuclease Eco31I (MBI-Fermentas, Vilnius, Lithuania) in 5 ml reaction buffer at 37° C. overnight. The reaction is stopped by heating to 70° C. The resulting mixture of nucleic acids is concentrated and treated with 20 U restriction endonuclease Eco31I and 100 U T7 DNA polymerase for one hour in the absence of desoxyribonucleotides. The resulting crude product is purified by chromatography on an anionic exchange column (Merck EMD-DMAE, sodium phosphate pH 7.0, 0–1 M NaCl) and obtained free of contamination by vector backbone, as assayed by PCR.

Example 3

1 mg of a preparation of plasmid pMOL-EGFp, obtained by employing the alkaline lysis procedure and the QiaPrep MaxiKit (Qiagen, Hilden, Germany) according to the instructions of the manufacturer, is reacted with 50 u each of enzymes Bsu15I, Eco32I and PstI in buffer Y+ (enzymes and buffer by Fermentas, Vilnius, Lithuania) at 37° C. overnight. After concentration, the reaction mixture is purified by anion exchange chromatography (as described in Examples 1 and 2 above). Host genomic DNA is determined by PCR amplification of host sequences and compared pre- and post-purification.

One feature of the invention resides broadly in a method for making a linear covalently closed double-stranded DNA molecule, comprising the steps of: amplification of the DNA double strand to be incorporated into the linear covalently closed double-stranded DNA molecule, as part of a construct that can be replicated in bacteria; isolation of the construct that can be replicated in bacteria, e.g., a plasmid; digestion of the plasmid with restriction endonucleases for primary digestion that recognize sequence sites contained within the linear covalently closed double-stranded DNA molecule, the restriction endonucleases for primary digestion chosen from enzymes that leave a single-stranded overlap on the resulting endonucleolytic plasmid fragments; ligation by a DNA ligase of the fragments obtained by the digestion with restriction endonucleases for primary digestion with short, hairpin-shaped oligodesoxyribonucleotides providing a single-stranded overlap hybridizing to the single-stranded overlap of the resulting endonucleolytic plasmid fragments, so that a covalently closed double-stranded DNA molecule forms; subsequent digestion of the resulting reaction mixture with a restriction endonuclease for secondary digestion, which recognizes and cuts a sequence provided by said plasmid but not within the part of the sequence forming said linear covalently closed double stranded DNA molecule; and a subsequent digestion with an enzyme providing an exonuclease activity specific for 3' ends of DNA and 5' ends of DNA.

Another feature of the invention resides broadly in the method where the linear covalently closed double-stranded DNA molecule is an expression construct consisting of a promoter sequence, a coding sequence, and a terminator sequence.

Yet another feature of the invention resides broadly in the method where the hairpin-shaped oligodesoxyribonucleotides provide a sequence in their stem that does not reconstitute a palindromic sequence upon ligation with the resulting endonucleolytic plasmid fragments, and where restriction endonucleases for primary digestion are present in the ligation reaction along with the ligase.

Still another feature of the invention resides broadly in the method where the restriction endonucleases for primary digestion are class-II restriction endonucleases, preferably members of the group BbsI, BbvI, BbvII, BpiI; BplI, BsaI, BsmAI, BsmBI, BsmFI, BspMI, Eam1104I, EarI, Eco31I, Esp3I, FokI, HgaI, SfaNI, or isoschizomers thereof.

A further feature of the invention resides broadly in a method for the purification of preparations of covalently closed DNA molecules, comprising a treatment of the preparation with exonucleolytic active enzymes specific for free 3' and 5' ends of DNA and a subsequent purification step to remove enzymes, buffer components and hydrolyzed desoxyribonucleotides.

Another feature of the invention resides broadly in a method for the purification of preparations of covalently closed DNA molecules, comprising a treatment of the preparation with restriction endonucleases that recognize and cut sequences not contained in the molecule to be purified and have a recognition site of no more than eight nucleotides, a treatment with exonucleolytic active enzymes specific for free 3' ends and 5' ends of DNA, and a subsequent purification step to remove enzymes, buffer components and hydrolyzed desoxyribonucleotides.

International Application No. PCT/EP99/04399, filed on Jun. 15, 1999, and Federal Republic of Germany Patent Application No. DE 198 26 758.4, filed on Jun. 15, 1998, and DE-OS 198 26 758.4 and DE-PS 198 26 758.4, as well as the published equivalents of all of the above patents, applications, or publications, and other equivalents or corresponding applications, if any, in corresponding cases in the Federal Republic of Germany and elsewhere, and the references cited in any of the documents cited herein, are hereby incorporated by reference as if set forth in their entirety herein.

U.S. patent application Ser. No. 09/310,842, filed on May 12, 1999, entitled "Design Principle for the Construction of Expression Constructs for Gene Therapy", having inventors Burghardt Wittig and Claas Junghans, and having assignee Soft Gene GmbH, Berlin, Federal Republic of Germany; Federal Republic of Germany Patent Application No. 196 48 625.4, filed on Nov. 13, 1996, and DE-OS 196 48 625.4 and DE-PS 196 48 625.4; and International Application No. PCT/DE97/02704, filed on Nov. 13, 1997, as well as the published equivalents of all of the above patents, applications, or publications, namely, WO 98/21322, published on May 22, 1998, and other equivalents or corresponding applications, if any, in corresponding cases in the Federal Republic of Germany and elsewhere, and the references cited in any of the documents cited herein, are hereby incorporated by reference as if set forth in their entirety herein.

U.S. patent application Ser. No. 09/358,499, filed on Jul. 21, 1999, entitled "Topologically Fixed, Matrix-Attached Nucleic Acid Molecule", having inventors Burghardt Wittig and Claas Junghans, ; Federal Republic of Germany Patent Application No. 197 53 182.2-44, filed on Nov. 21, 1997, having inventors Burghardt Wittig and Claas Junghans, and DE-OS 197 53 182.2-44 and DE-PS 197 53 182.2-44; and International Application No. PCT/DE98/03466, filed on Nov. 19, 1998, as well as the published equivalents of all of the above patents, applications, or publications, namely, WO 98/21322, published on May 22, 1998, and other equivalents or corresponding applications, if any, in corresponding cases in the Federal Republic of Germany and elsewhere, and the references cited in any of the documents cited herein, are hereby incorporated by reference as if set forth in their entirety herein.

International Patent Application No. PCT/US92/11076, having International Filing Date Dec. 17, 1992, having International Publication Number WO 93/13216, having International Publication Date Jul. 8, 1993, entitled "Site-Directed Mutagenesis of DNA", having inventors Nickoloff et al., as well as the published equivalents of all of the above patents, applications, and publications, are hereby incorporated by reference as if set forth in their entirety herein.

International Patent Application No. PCT/US92/00540, having International Filing Date Jan. 22, 1992, having International Publication No. WO 92/13963, entitled "Method for Preparation of Closed Circular DNA", having inventor Hyman, as well as the published equivalents of all of the above patents, applications, and publications, are hereby incorporated by reference as if set forth in their entirety herein.

Some examples of cleavage, ligation, and hybridization methods and materials therefor that may be used or adapted for use in at least one possible embodiment of the present invention may be found in the following U.S. patents and other publications: U.S. Pat. No. 6,001,567, issued to inventors Brow et al. on Dec. 14, 1999; U.S. Pat. No. 5,994,069, issued to inventors Hall et al. on Nov. 30, 1999; U.S. Pat. No. 5,985,557, issued to inventors Prudent et al. on Nov. 16, 1999; U.S. Pat. No. 5,925,525, issued to inventors Fodor et al. on Jul. 20, 1999; U.S. Pat. No. 5,910,408, issued to inventors Szostak et al. on Jun. 8, 1999; U.S. Pat. No. 5,888,780, issued to inventors Dahlberg et al. on Mar. 30, 1999; U.S. Pat. No. 5,849,485, issued to inventors Sladek et al. on Dec. 15, 1998; U.S. Pat. No. 5,846,717, issued to inventors Brow et al. on Dec. 8,1998; U.S. Pat. No. 5,843,669, issued to inventors Kaiser et al. on Dec. 1, 1998; U.S. Pat. No. 5,843,654, issued to inventors Heisler et al. on Dec. 1, 1998; U.S. Pat. No. 5,831,065, issued to inventor Brenner on Nov. 3, 1998; U.S. Pat. No. 5,800,992, issued to inventors Fodor et al. on Sep. 1, 1998; U.S. Pat. No. 5,719,028, issued to inventors Dahlberg et al. on Feb. 17, 1998; U.S. Pat. No. 5,714,330, issued to inventors Brenner et al. on Feb. 3, 1998; U.S. Pat. No. 5,495,006, issued to inventors Climie et al. on Feb. 27, 1996; and U.S. Pat. No. 4,808,525, issued to inventors McClelland et al. on Feb. 28, 1989, as well as the following publications: Sigman et al., "Chemical Nucleases," Chem. Rev. 93:225 (1993); Hiraro et al., "Most Compact Hairpin-Turn Structure Exerted by a Short DNA Fragment, d(GCGAAGC) in Solution: An Extraordinarily Stable Structure Resistant to Nucleases and Heat," Nucl. Acids Res. 22(4):576 (1994): Longley et al., "Characterization of the 5' to 3' Exonuclease Associated with Thermus aquaticusDNA Polymerases," Nucl. Acids Res. 18:7317 (1990); Engelke, "Purification of Thermus aquaticus DNA Polymerase Expressed in Escherichia coli," Anal. Biochem. 191:396 (1990); Lyamichev et al., "Structure-Specific Endonucleolytic Cleavage of Nucleic Acids by Eubacterial DNA Polymerase," Science 260:778 (1993); Copley and Boot, "Exonuclease Cycling Assay: An Amplified Assay for the Detection of DNA Sequences," BioTechniques 13:888 (1992); and Ito et al., "Compilation and Alignment of DNA Polymerase Sequences," Nucl. Acids Res. 19:4045 (1991).

Some examples of purification materials, apparatus, and methods that may be used or adapted for use in at least one possible embodiment of the present invention may be found in the following U.S. Pat. No. 4,794,075, issued to inventors Ford et al. on Dec. 27, 1988; U.S. Pat. No. 5,815,477, issued to inventors Williams et al. on Sep. 29, 1998; and U.S. Pat. No. 5,712,088, issued to inventors Houghton et al. on Jan. 27, 1998.

Some examples and descriptions of isolation methods, vector gene therapy, plasmid formation, expression cassettes, and expression constructs and amplification methods that may be used or adapted for use in at least one possible embodiment of the present invention may be found in the following U.S. patents and other publications: U.S. Pat. No. 5,998,174, issued to inventors Glorioso et al. on Dec. 7, 1999; U.S. Pat. No. 5,998,152, issued to inventors Lynch et al. on Dec. 7, 1999; U.S. Pat. No. 5,981,190, issued to inventor Israel on Nov. 9, 1999; U.S. Pat. No. 5,952,201, issued to inventors Landegren et al. on Sep. 14, 1999; U.S. Pat. No. 5,925,525, issued to inventors Fodor et al. on Jul. 20, 1999; U.S. Pat. No. 5,919,665, issued to inventor Williams on Jul. 6, 1999; U.S. Pat. No. 4,794,075, issued to inventors Ford et al. on Dec. 27, 1988; U.S. Pat. No. 5,830,705; U.S. Pat. No. 5,827,704, issued to inventors Cease et al. on Oct. 27, 1998; U.S. Pat. No. 5,800,992, issued to inventors Fodor et al. on Sep. 1, 1998; U.S. Pat. No. 5,712,088, issued to inventors Houghton et al. on Jan. 27, 1998; U.S. Pat. No. 5,683,909; U.S. Pat. No. 5,621,080; U.S. Pat. No. 5,455,029, issued to inventors Hartman et al. on Oct. 3, 1995; U.S. Pat. No. 5,441,885, issued to inventors Goldberg et al. on Aug. 15, 1995; U.S. Pat. No. 5,436,138, issued to inventors Duronio et al. on Jul. 25, 1995; No. 5,376,527; U.S. Pat. No. 5,266,491, issued to inventors Nagata et al. on Nov. 30, 1993; U.S. Pat. No. 4,948,731, issued to inventors Gehrke et al. on Aug. 14, 1990; and U.S. Pat. No. 4,460,689, as well as the following publications: Barany, "Genetic Disease Detection and DNA Amplification Using Cloned Thermostable Ligase," Proc. Natl. Acad. Sci. 88:189 (1991); Landgren, "Molecular Mechanics of Nucleic Acid Sequence Amplification," Trends in Genetics 9:199 (1993); Mullis, "The Polymerase Chain Reaction in an Anemic Mode: How to Avoid Cold Oligodeoxyribonuclear Fusion," PCR Methods Applic. 1:1 (1991); Marmur and Lane, "Strand Separation and Specific Recombination in Deoxyribonucleic Acids: Biological Studies," Proc. Natl. Acad. Sci. USA 46:461 (1960); Doty et al., "Strand Separation and Specific Recombination in Deoxyribonucleic Acids: Physical Chemical Studies," *Proc. Natl. Acad. Sci. USA* 46:461 (1960); Kornberg, *DNA Replication*, W. H. Freeman and Co., San Francisco (1980); Gelfand, *PCR Technology*—Principles and Applications for DNA Amplification (H. A. Erlich, ed.), Stockton Press, New York (1989); and Antao et al., "A Thermodynamic Study of Unusually Stable DNA and RNA Hairpins," *Nucl. Acids. Res.* 19:5901 (1991).

Some examples of genetic vaccination methods, procedures, materials, and/or apparatus that may be used or adapted for use in at least one possible embodiment of the present invention may be found in the following U.S. Pat. Nos. 5,889,038; 5,880,103; U.S. Pat. No. 5,869,058; U.S. Pat. No. 5,886,553; U.S. Pat. No. 5,861,397; U.S. Pat. No. 5,861,290; U.S. Pat. No. 5,859,324; U.S. Pat. No. 5,840,707; U.S. Pat. No. 5,837,511; U.S. Pat. No. 5,837,510; U.S. Pat. No. 5,837,269; U.S. Pat. No. 5,830,876; U.S. Pat. No. 5,817,637; U.S. Pat. No. 5,780,448; U.S. Pat. No. 5,776,889; U.S. Pat. No. 5,738,852; U.S. Pat. No. 5,736,524; U.S. Pat. No. 5,891,432; U.S. Pat. No. 5,889,156; U.S. Pat. No. 5,888,814; U.S. Pat. No. 5,888,502; U.S. Pat. No. 5,882,640; U.S. Pat. No. 5,879,675; U.S. Pat. No. 5,874,077; U.S. Pat. No. 5,861,164; U.S. Pat. No. 5,853,765; U.S. Pat. No. 5,849,586; U.S. Pat. No. 5,846,526; U.S. Pat. No. 5,837,510; U.S. Pat. No. 5,837,246; U.S. Pat. No. 5,830,876; U.S. Pat. No. 5,830,458; U.S. Pat. No. 5,830,456; U.S. Pat. No. 5,824,300; U.S. Pat. No. 5,817,637; U.S. Pat. No. 5,817,307; U.S. Pat. No. 5,804,191; U.S. Pat. No. 5,804,187; U.S. Pat. No. 5,780,304; U.S. Pat. No. 5,776,459; U.S. Pat. No. 5,766,625; U.S. Pat. No. 5,759,535; U.S. Pat. No. 5,753,262; U.S. Pat. No. 5,753,258; U.S. Pat. No. 5,753,258; U.S. Pat. No. 5,736,139; U.S. Pat. No. 5,728,385; U.S. Pat. No. 5,723,283; and U.S. Pat. No. 5,861,290.

For illustrative methodology relating to molecular biology techniques, U.S. Pat. No. 5,866,551 is incorporated herein by reference. These techniques include, for example, preparative extractions of plasmid DNA, centrifugation of plasmid DNA in a cesium chloride gradient, agarose or acrylamide gel electrophoresis, purification of DNA fragments by electroelution, phenol or phenol-chloroform extraction of proteins, transformation in Escherichia coli, and precipitation of DNA in saline medium. Examples of such techniques may be found in Sambrook et al., *Molecular Cloning: A Laboratory Manual*, 2d ed., Cold Spring Harbor Laboratory, Cold Spring Harbor, New York, 1989; Ausubel, M. et al. (eds.), *Current Protocols in Molecular Biology*, John Wiley & Sons, New York, 1987. For illustrative methodology relating to amplification of DNA fragments by the polymerase chain reaction (PCR) technique, see Mullis, K. B. and Faloona, F. A., "Specific Synthesis of DNA in Vitro via a Polymerase-Catalyzed Chain Reaction," *Methods in Enzymology* 155:335–350 (1987) and Saiki, R. K. et al., *Science* 230:1350–1354 (1985).

Some examples of promoters or polyadenylation signals that may be used or adapted for use in at least one possible embodiment of the present invention may be found in U.S. Pat. No. 5,593,972, issued to inventors Weiner et al. on Jan. 14, 1997.

Further explanations of abbreviations and/or methods and materials referenced herein may be found in the following publications: *Gale Encyclopedia of Medicine*, vol. 3, published by Gale Research, 1999; Health Reference Series, vol. 13: Genetic Disorders, published by Frederick G. Ruffner, Jr., 1996; *Encyclopedia of Molecular Biology and Molecular Medicine*, edited by Robert A. Meyers, published by VCH Publishers, New York, 1996; *Dictionary of Gene Technology*, edited by Gunther Kahl, published by VCH Publishers, New York, 1995; *Dictionary of Genetics*, 5th edition, edited by Robert C. King, published by Oxford University Press, New York, 1997; *Encyclopedia of Human Biology*, edited by R. Dulbecco, published by Academic Press, New York, 1997; and *Biology*, by E. Solomon, L. Berg, D. Martin, and C. Villee, published by Saunders College Publishing, Harcourt Brace College Publishers, 1993.

Some of the materials and apparatus that may be needed to perform procedures or methods relating to at least one embodiment of the present invention, which materials and apparatus may include, for example, gene lines, plasmids, cloning vectors, cell culture media, DNA, and reagents, may be obtained from American Type Culture Collection (ATCC), 10801 University Blvd., Manassas, Va. 20110-2204; New England Biolabs, Massachusetts; Bio-Lab LTD, Industrial Area Atarot, P.O.B. 34038, Jersualem 91340, Israel; International Biotechnologies Inc., New Haven, Conn. 06535; Molecular Biology Institute (MBI), La Jolla, Calif. 92037; and/or MBI-Fermentas, Vilnius, Lithuania.

The manufacturers' instructions, directions, specifications, and/or laboratory manuals for all of the apparatus and materials referenced herein are incorporated by reference into this specification.

As used herein, including the claims appended hereto, the following terms mean:

A cassette is any polynucleotide sequence having an identifiable structure. A cassette can comprise a vector or a component of a vector. A cassette can include one or more nucleic acid sequence. An example of a cassette is a sequence containing a promoter element, one or more nucleic acid sequences for expression, and a polyadenylation sequence.

A polynucleotide is any portion of a nucleic acid molecule that is identified by a specific sequence of nucleotides.

A polynucleotide is expressed if it is transcribed into an RNA transcript.

A restriction site is a DNA sequence, as well as any degenerate variation of that sequence, to which a particular restriction endonuclease binds with relative specific affinity.

A vector is any polynucleotide competent for introducing one or more exogenous nucleic acid sequences into a cellular environment.

A promoter is a polynucleotide required for transcription at significant levels of a second polynucleotide to which it is operably linked. Operably linked means that separate nucleic acid sequences are functionally associated such that an event at one can precipitate a response from another. Two or more operably linked nucleic acid sequences can, in combination, comprise an independent genetic element, such as an expression cassette.

In this application, it is hereby noted that the prefix "desoxy-" can be a form of the prefix "deoxy-".

The components disclosed in the various publications, disclosed or incorporated by reference herein, may be used in at least one possible embodiment of the present invention, as well as equivalents thereof.

The drawings are incorporated by reference in their entirety into this specification.

All, or substantially all, of the components and methods of the various embodiments may be used with at least one embodiment or all of the embodiments, if more than one embodiment is described herein.

All of the patents, patent applications, and publications recited herein, and in the Declaration attached hereto, are hereby incorporated by reference as if set forth in their entirety herein.

The corresponding foreign and international patent publication applications, namely, Federal Republic of Germany Patent Application No. DE 198 26 758.4, filed on Jun. 15, 1998, having inventors Prof. Dr. Burghardt Wittig, Claas Junghans, and Matthias Schroff, and DE-OS 198 26 758.4 and DE-PS 198 26 758.4 and International Application No. PCT/EP99/04339, as well as their published equivalents, and other equivalents or corresponding applications, if any, in corresponding cases in the Federal Republic of Germany and elsewhere, and the references cited in any of the documents cited herein, are hereby incorporated by reference as if set forth in their entirety herein.

The details in the patent, patent applications, and publications may be considered to be incorporable, at Applicants' option, into the claims during prosecution as further limitations in the claims to patentably distinguish any amended claims from any applied prior art.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function clauses are intended to cover the structures described herein as performing the recited function and not only structural equivalents but also equivalent structures.

The invention as described hereinabove in the context of the preferred embodiments is not to be taken as limited to all of the provided details thereof, since modifications and variations thereof may be made without departing from the spirit and scope of the invention.

The sequence listing is attached hereafter on pages 22–25 and constitutes part of this application.

What is claimed is:

1. A method for obtaining a non-circular covalently closed double-stranded DNA molecule, the method comprising:
    (a) providing a first composition comprising a double-stranded DNA comprising a target DNA sequence;
    (b) excising the target DNA sequence from the DNA with an endonuclease to provide a second composition comprising the target DNA sequence;
    (c) providing a third composition comprising:
        (i) the target DNA sequence and
        (ii) one or more hairpin-shaped oligodesoxyribonucleotide(s);
    (d) ligating 3' and 5' strands of a hairpin-shaped oligodesoxyribonucleotide of (c) to respective ends of 3' and 5' strands of the target DNA sequence to provide a fourth composition comprising a mixture of:
        (i) covalently closed double-stranded DNA comprising the target sequence, and
        (ii) unligated contaminating nucleic acid material;
    (e) digesting components of the fourth composition in the presence of nucleases having affinity only for the contaminating nucleic acid material to provide a fifth composition comprising:
        (i) the covalently closed double-stranded DNA comprising the target sequence, and
        (ii) at least partially digested contaminating nucleic acid material, which is separable from the covalently closed double-stranded DNA comprising the target sequence by at least one physical or chemical characteristic comprising size; and
    (f) separating the covalently closed double-stranded DNA comprising the target sequence from one or more other components of the fifth composition to provide a sixth composition comprising the covalently closed double-stranded DNA, which sixth composition is substantially free of contaminating nucleic acid material,
    wherein any of steps (a) to (e) are temporally related in any manner that results in the formation of the fifth composition.

2. The method according to claim 1, wherein step (f) comprises a size separation step selected from the group consisting of chromatographic separation, centrifugation, filtration, and combinations thereof.

3. The method of claim 1 wherein the covalently closed double-stranded DNA molecule is unbranched.

4. The method according to claim 1, wherein the DNA comprising the target sequence is selected from the group consisting of:
   (A) DNA configured to replicate in at least one species of bacterium;
   (B) DNA selected from the group consisting of plasmids, cosmids and phagemids; and
   (C) DNA comprising an expression construct comprising:
      (i) a promotor sequence;
      (ii) a coding sequence; and
      (iii) a terminator sequence.

5. The method according to claim 4, wherein step (a) comprises amplifying the DNA comprising the target DNA sequence by culturing bacteria comprising the DNA comprising the target DNA sequence.

6. The method of claim 1 wherein step (b) comprises digesting the DNA comprising the target DNA sequence with one or more restriction endonucleases selected to excise the target DNA sequence.

7. The method according to claim 6, wherein:
   (i) at least one of the restriction endonuclease(s) is selected to leave at least one single-stranded overlap on the target DNA sequence; and
   (ii) the one or more hairpin-shaped oligodesoxyribonucleotide(s) comprise a single-stranded overlap configured to hybridize to the at least one single-stranded overlap on the target DNA sequence.

8. The method according to claim 7, wherein the overlap is at least three nucleotides in length.

9. The method of claim 1 wherein step (d) comprises using at least one DNA ligase to ligate the hairpin-shaped oligodesoxyribonucleotides to the target DNA sequence.

10. The method according to claim 1, wherein step (e) comprises digesting components of the fourth composition with at least one restriction endonuclease recognizing the contaminating nucleic acid material and not the covalently closed double-stranded DNA.

11. The method of claim 1, wherein step (e) comprises digesting components of the fourth composition with an exonuclease.

12. The method of claim 11, wherein the exonuclease comprises bacteriophage T4 and/or T7 DNA polymerase.

13. The method according to claim 11, wherein step (e) comprises digesting components of the fourth composition with an endonuclease.

14. The method according to claim 1, wherein step (e) comprises the following steps, performed simultaneously or sequentially in any order:
   (i) digesting components of the fourth composition with a restriction endonuclease recognizing only the non-covalently closed double-stranded DNA in the composition; and
   (ii) digesting components of the fourth composition with an exonuclease.

15. The method of claim 1 wherein step (d) does not result in the formation of a palindromic sequence.

16. The method according to claim 1, wherein the hairpin-shaped oligodesoxyribonucleotides are provided with a non-palindromic overlap configured so that the hairpin-shaped oligodesoxyribonucleotides cannot be ligated to each other.

17. The method of claim 1 wherein step (d) results in a site that cannot be cut using the endonuclease used to excise the target DNA sequence in step (b).

18. The method according to claim 17, wherein step (e) further comprises redigesting any hairpin dimers and/or polymeric dimers formed in the partially digested contaminating nucleic acid material, using an endonuclease selected to cut the dimers, which endonuclease does not cut the non-covalently closed double-stranded DNA.

19. The method according to claim 17, wherein:
   (a) the endonuclease used to excise the target DNA sequence comprises EcoRI;
   (b) the hairpin-shaped oligodesoxyribonucleotide comprises a double-stranded stem ending with a single-stranded overlap at the 5' end and comprising the sequence AATTG, wherein:
      (iv) AATT of the AATTG sequence is the single-stranded overlap; and
      (v) G of the AATTG sequence is the first base of the double-stranded stem; and
   (c) ligation of the target DNA sequence to the hairpin-shaped oligodesoxyribonucleotide results in covalently closed double-stranded DNA that cannot be cut by EcoRI.

20. The method according to claim 1, wherein the endonuclease in step (b) comprises at least one restriction endonuclease selected from the group consisting of:
   (i) the group consisting of BbsI, BbvI, BbvII, BpiI, BplI, BsaI, BsmAI, BsmBI, BsmFI, BspMI, Eam1104I, EarI, Eco31I, Esp3I, FokI, HgaI, SfaNI;
   (ii) the group consisting of class II restriction endonucleases not listed in (i); and
   (iii) the group consisting of isoschizomers of (i) and (ii).

21. A method for preparing a substantially pure preparation of non-circular covalently closed DNA molecules, the method comprising:
   (a) treating a composition comprising the covalently closed DNA molecules and contaminating components with at least one exonucleolytic active enzyme having specificity for free 3' ends of DNA and/or 5' ends of DNA; and
   (b) separating from the non-circular covalently closed DNA molecules one or more contaminating components.

22. The method according to claim 21, wherein the one or more contaminating components are selected from the group consisting of enzymes, buffer components, and hydrolyzed desoxyribonucleotides.

23. A method of producing a covalently closed DNA dumbbell-shaped construct from a DNA comprising a target DNA, said method comprising the steps of:
   (a) excising the target DNA sequence from the DNA comprising the target DNA by restriction digestion;
   (b) ligating the target DNA sequence to hairpin oligodesoxyribonucleotides to form a composition comprising a covalently closed DNA dumbbell-shaped construct, and unligated contaminating polymeric DNA molecules;
   (c) digesting the composition formed in (b) with endonucleolytic enzymes and exonucleolytic enzymes to substantially degrade substantially all contaminating polymeric DNA molecules, without substantially degrading the covalently closed DNA dumbbell-shaped construct; and
   (d) separating the covalently closed DNA dumbbell-shaped construct from the substantially degraded contaminating polymeric DNA molecules.

* * * * *